United States Patent
Buch et al.

(10) Patent No.: US 12,245,741 B2
(45) Date of Patent: Mar. 11, 2025

(54) METHODS, SYSTEMS, AND COMPUTER READABLE MEDIA FOR GENERATING AND PROVIDING ARTIFICIAL INTELLIGENCE ASSISTED SURGICAL GUIDANCE

(71) Applicant: The Trustees of the University of Pennsylvania, Philadelphia, PA (US)

(72) Inventors: Vivek Paresh Buch, Philadelphia, PA (US); Peter John Madsen, Philadelphia, PA (US); Jianbo Shi, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 1083 days.

(21) Appl. No.: 17/263,025

(22) PCT Filed: Jul. 25, 2019

(86) PCT No.: PCT/US2019/043428
§ 371 (c)(1),
(2) Date: Jan. 25, 2021

(87) PCT Pub. No.: WO2020/023740
PCT Pub. Date: Jan. 30, 2020

(65) Prior Publication Data
US 2021/0307841 A1    Oct. 7, 2021

Related U.S. Application Data

(60) Provisional application No. 62/703,400, filed on Jul. 25, 2018.

(51) Int. Cl.
*A61B 1/00* (2006.01)
*A61B 5/00* (2006.01)
(Continued)

(52) U.S. Cl.
CPC ........ *A61B 1/000096* (2022.02); *A61B 5/489* (2013.01); *A61B 5/4893* (2013.01);
(Continued)

(58) Field of Classification Search
CPC . A61B 1/000096; A61B 5/489; A61B 5/4893; A61B 5/7267; A61B 5/7275;
(Continued)

(56) References Cited

U.S. PATENT DOCUMENTS 5,882,206 A    3/1999 Gillio
9,280,913 B2   3/2016 Peters et al.
(Continued)

FOREIGN PATENT DOCUMENTS

WO    WO-2018/058509 A1    4/2018

OTHER PUBLICATIONS

Semantic Segmentation (Semantic Segmentation using Fully Convolutional Networks over the years, Jun. 1, 2017; https://meetshah. dev/semantic-segmentation/deep-learning/pytorch/visdom/2017/06/01/semantic-segmentation-over-the-years.*
(Continued)

*Primary Examiner* — Bo Joseph Peng
(74) *Attorney, Agent, or Firm* — Jenkins, Taylor & Hunt, P.A.

(57) ABSTRACT

A method for generating and providing artificial intelligence assisted surgical guidance includes analyzing video images from surgical procedure and training a neural network to identify at least one of anatomical objects, surgical objects, and tissue manipulation in video images. The method includes receiving, by the neural network, a live feed of video images from the surgery. The method further includes classifying, by the neural network, at least one of anatomical objects, surgical objects, and tissue manipulation in the live feed of video images. The method further includes output-
(Continued)

ting, in real time, surgical guidance based on algorithms created using the classified at least on of anatomical objects, surgical objects, and tissue manipulations in the live feed of video images.

9 Claims, 7 Drawing Sheets

(51) Int. Cl.
  *A61B 34/20* (2016.01)
  *G06V 10/764* (2022.01)
  *G06V 10/82* (2022.01)
  *G06V 20/20* (2022.01)
  *A61B 90/00* (2016.01)

(52) U.S. Cl.
  CPC .......... *A61B 5/7267* (2013.01); *A61B 5/7275* (2013.01); *A61B 5/749* (2013.01); *A61B 34/20* (2016.02); *G06V 10/764* (2022.01); *G06V 10/82* (2022.01); *G06V 20/20* (2022.01); *A61B 2034/2065* (2016.02); *A61B 2034/2068* (2016.02); *A61B 2090/365* (2016.02)

(58) Field of Classification Search
  CPC . A61B 5/749; A61B 34/20; A61B 2034/2065; A61B 2034/2068; A61B 2090/365; A61B 1/313; G06V 10/764; G06V 10/82; G06V 20/20; G06V 2201/031; G06F 18/2413; G16H 30/40; G16H 50/20
  See application file for complete search history.

(56) References Cited

U.S. PATENT DOCUMENTS

| | | |
|---|---|---|
| 9,589,374 B1 | 3/2017 | Gao et al. |
| 9,754,371 B2 | 9/2017 | Kateb et al. |
| 2013/0038707 A1 | 2/2013 | Cunningham et al. |
| 2016/0259888 A1 | 9/2016 | Liu et al. |
| 2016/0284084 A1* | 9/2016 | Gurcan .................. G16H 30/40 |
| 2017/0360412 A1 | 12/2017 | Rothberg et al. |
| 2019/0262084 A1* | 8/2019 | Roh ....................... G16H 20/40 |

OTHER PUBLICATIONS

Mann et al. (Segmentation of retinal blood vessels using artificial neural networks for early detection of diabetic retinopathy, AIP Conf. Proc. 1836, 020026 (2017).*

Notification of Transmittal of the International Search Report and the Written Opinion of the International Searching Authority, or the Declaration for International Application No. PCT/US2019/043428 (Oct. 11, 2019).

Communication of European publication number and information on the application of Article 67(3) EPC for European Patent Application No. 19841186.0 (May 6, 2021).

"Robotix Mentor," 3D Systems, formerly Simbionix, pp. 1-2 (2017).

"Verb Surgical Delivers Digital Surgery Prototype Demonstration to Collaboration Partners," Verb Surgical, The Wayback Machine, Verb Surgical Delivers Digital Surgery Prototype Demonstration to Collaboration Partners | Verb Surgical (archive.org), pp. 1-4 (Jan. 26, 2017).

Strickland, "Autonomous Robot Surgeon Bests Humans in World First," The Human OS, Robotics, Medical Robots, pp. 1-4 (May 4, 2016).

Whittaker et al., "Validation of the Robotix Mentor Robotic Surgery Simulator," Journal of Endourology, vol. 30, No. 3, pp. 1-10 (Mar. 2016).

Shademan et al., "Supervised autonomous robotic soft tissue surgery," Science Transitional Magazine, vol. 8, Issue 337, pp. 1-9 (May 4, 2016).

Alam et al., "Emerging Intraoperative Imaging Modalities to Improve Surgical Precision", Intraoperative imaging Modalities, pp. 1-11 (Jun. 18, 2018).

European search report pursuant to Rule 62 EPC for European Patent Application 19841186.0 (Mar. 21, 2022).

Office Action for European Patent Application Serial No. 19841186.0 (Feb. 27, 2024).

* cited by examiner

METHODS, SYSTEMS, AND COMPUTER READABLE MEDIA FOR GENERATING AND PROVIDING ARTIFICIAL INTELLIGENCE ASSISTED SURGICAL GUIDANCE

PRIORITY CLAIM

This application claims the benefit of U.S. Provisional Patent Application Ser. No. 62/703,400, filed Jul. 25, 2018, the disclosure of which is incorporated herein by reference in its entirety.

TECHNICAL FIELD

The subject matter described herein relates to providing surgical guidance. More particularly, the subject matter described herein relates to methods, systems, and computer readable media for generating and providing artificial intelligence assisted surgical guidance.

BACKGROUND

Artificial Intelligence (AI) technology is transforming the way we live. Autonomous cars, touchless cleaning robots, and personal assistants, such as 'Alexa', 'Siri', 'Cortana', and 'Google' are ushering humanity into a new world order. Heavy investments in this technology by the most influential companies of the current century have led to exponential growth in this industry over the past two to three years. One of the primary launching pads for expanding AI technology came from the famous IBM super computer known as Watson. Watson has since been recruited in the medical field to help physicians create differential diagnostic algorithms. As medical knowledge and disease states increase in complexity, the ability for the human brain to accurately identify and diagnose patients becomes increasingly difficult. In surgery, however, AI systems have not yet been readily applied. This is primarily due to the fact that until recently, machine learning technology was not powerful enough to be utilized in the surgical realm. However, the advent of computer vision framed within deep neural networks (DNNs), has significantly enhanced the capability of AI systems.

Accordingly, there exist a need for methods, systems, and computer readable media for generating and providing AI-assisted surgical guidance.

SUMMARY

A method for generating and providing artificial intelligence assisted surgical guidance includes analyzing video images from surgical procedures and training a neural network to identify at least one of anatomical objects (i.e. tissue types and critical structures), surgical objects (i.e. instruments and items), and tissue manipulation (i.e. the precise interface of anatomical and surgical objects) in video images. The method includes a process by which the data is further grouped by surgery type and the neural network is trained on patterns in chronological and/or positional relationships between at least one of anatomical objects, surgical objects, and tissue manipulation during the course of each procedure. The method subsequently includes receiving, by the neural network, a live feed of video images from the surgery. The method further includes classifying, by the neural network, at least one of anatomical objects, surgical objects, and tissue manipulation in the live feed of video images. The method further includes outputting, in real time, by audio and video-overlay means, tailored surgical guidance based on the classified at least one of anatomical objects, surgical objects, and tissue manipulations in the live feed of video images.

The subject matter described herein can be implemented in software in combination with hardware and/or firmware. For example, the subject matter described herein can be implemented in software executed by a processor. In one exemplary implementation, the subject matter described herein can be implemented using a non-transitory computer readable medium having stored thereon computer executable instructions that when executed by the processor of a computer control the computer to perform steps. Exemplary computer readable media suitable for implementing the subject matter described herein include non-transitory computer-readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

The subject matter described herein will now be explained with reference to the accompanying drawings of which.

DETAILED DESCRIPTION

Every moment of a surgical procedure is defined by a decision. Some of these decisions will be mundane, but others require expert judgement and can alter a surgery's course, its outcome, and ultimately a patient's life. When distilled to its core, mastery in surgery requires the precise execution of intricate motor tasks and an ability to expertly analyze the operative field to correctly make these important decisions. The former is a skillset that is driven by human control. The latter, however, is dependent upon pattern recognition. No amount of physical operative talent can overcome surgical experience because the experienced surgeon is better at recognizing patterns in their operative environment. However, even the most experienced surgeons face many difficult decisions during crucial surgical checkpoints. The subject matter described herein includes a technology that can assist surgeons in real-time to recognize objects in their operative environment, notify them of situations that may require additional caution prior to executing an action, and assist surgeons in crucial decision-making situations.

Though the human brain is arguably the most complex machine ever created, Artificial Intelligence technology is transforming the way we live. In recent years, advancements in machine learning have led to the development of deep neural networks (DNNs), which have been able to consistently outperform the human brain in computational speed and, most importantly, pattern recognition. Our technology, the Artificial Operative Assistant (AOA), applies these advancements to the field of surgery to enhance decision-making and usher in the artificial intelligence revolution in surgery. The AOA provides real-time automated feedback on the surgical field to augment a surgeon's decision making and has the potential to become essential to any surgical procedure, constituting a new gold standard. Current work in this field has focused mostly on developing augmented reality systems that can overlay registered pre-operative imaging on an operative field to guide surgery or using computer vision technology to improve robotic surgery. Our technology is fundamentally different and novel, because it has the potential to be seamlessly adaptable to any surgery and is not dependent upon registration of imaging (a process that can be fraught with its own complications and difficulties) or restricted to robot-assisted procedures.

As a product, we would aim to launch our platform, known as TAIRIS, through either a cloud based or physical server. The end user-interface will be known as the AOA. Cloud based access would entail video feed processing in the cloud (in a HIPPA compliant manner) and results returned to the OR either through a boom audiovisual monitor or to a worn heads-up display. The computing power involved may prohibit this so we will also be prepared to create a physical processing device (local DNN CPU, with daily updates/communication between itself and the mainframe TAIRIS server) that can be integrated into an individual or suite of ORs. Either of these methods would require an initial purchase from a hospital or surgical group to integrate the system and we would also collect subscription fees that allow users to obtain updated and improved network processing as TAIRIS is continuously trained by end-user feedback.

In its first iteration, our technology utilizes computer vision based DNNs to continuously monitor an operative field and provide feedback to a surgeon in real-time with the goal of enhancing surgical decision making. In all operations, a video feed of the operative field can be obtained with either an overhead operating room (OR) camera, microscope, or endoscope. Regardless of the video input, the feed will be analyzed on a trained, multilayer, convolutional deep neural network capable of identifying key anatomical objects, surgical objects, and tissue manipulation. This real-time feedback and output of the trained DNN is considered the Artificial Operative Assistant (AOA).

To begin building this system, we will perform video processing on readily available microscopic and endoscopic recordings of cranial and spinal neurosurgical cases. Off-line image segmentation and labeling will be performed to break down components of representative video frames into matrices containing pixel-by-pixel categorizations of select anatomical and surgical objects. For example, in a lumbar microdiscectomy operation the pathological process involves a herniated lumbar intervertebral disc that is causing nerve root impingement resulting in pain, numbness, paresthesia, and weakness. The operation is performed with a small incision and a microscope to uncover the impinged nerve root and remove herniated disc material. Very often the distinction between nerve root and herniated disc is not clear. A few key categories can be identified in the microscopic recording of the operation including bone, ligament, thecal sac, nerve root, and disc. Images from this procedure will be labeled with these defined structures and then will be fed into our DNN.

Once initialized, this network will be trained using hundreds of these de-identified surgical videos in which the same key structures have been segmented out. Over multiple iterations, the deep neural network will coalesce classifiers for each pixel designating the anatomical or surgical object class to which it belongs. These DNN classifiers will then be utilized on-line to predict the most likely object class for each pixel during real-time video. Once this classifier can be verified for accuracy, it can be implemented during novel video capture. This output, namely the identified key elements of the surgical field, can then be returned to the surgeon in audiovisual from on a monitor or, in the future, a heads-up augmented reality display in real-time. This will appear as segmented overlays over the specific anatomic structures and provide probability estimates for each item to demonstrate the AOA's level of certainty (or uncertainty).

This foundational information and feedback will provide guidance to the surgeon as questions or uncertainty arise in the case. In this example, the trained DNN will be able to identify with some weighted probability what elements of the operative field belong to the nerve root versus disc material class. This concept can be extrapolated to any surgery. We plan to use multiple types of surgery to train the network to improve generalizability of the output to many surgical scenarios. Also, general labeling (i.e. "bone", "muscle", "blood vessel", etc.) will help to keep the scope of the network broad and capable of being used in many different types of surgery and even novel future applications.

Classifiers will also be set up to include tissue manipulation thresholds. By using contour detection techniques, we can actively monitor manipulation of key anatomic objects. This could be utilized to help determine potentially risky maneuvers prior to execution. For example, by defining the amount of manipulation an identified object can tolerate, the AOA will be able to provide feedback to the surgeon if they have or are about to exceed a safe level of manipulation. The AOA will also be able to caution surgeons if they are approaching structures designated as "do not manipulate," such as spinal cord during intradural spine surgery or the posterior capsule of the lens in cataract surgery.

In our second iteration, chronological and positional relationships between anatomical objects, surgical objects, and tissue manipulation over the course of a procedure will be entrained by the network. Quantifying these relationships will enable real-time object tracking and feedback for surgeons regarding normal stepwise procedure flow (chronological relationships) and upcoming "hidden" objects (positional relationships). The surgical guidance generator will utilize the foundational information from the neural network output as described above. This data will also be post-processed in a novel hierarchical algorithm framework and combined with other input data such as pre-operative imaging, patient demographic and co-morbidity factors, surgical object cost data, or intraoperative vital signs. These post-processed outputs of the surgical guidance generator will be clinically tailored, surgery- and even surgeon-specific including information such as a surgical roadmap of suggested next steps, movement efficiency metrics, complication avoidance warnings, procedural stepwise cost estimates, and predictive analytics that can provide novel intraoperative indices predicting post-operative outcome.

Furthermore, development of a graphical user interface will enable intra-operative and post-operative feedback on the AOA output accuracy which can be fed back into the DNN and allow for continuous training and propagation of the DNN. Post-operatively, the surgeon can be fed images onto a mobile device or tablet from the previous surgery where the AOA had some level of uncertainty about an object. The surgeon would provide feedback about the object and about the AOA's output about the object. This information can be fed back into the DNN to improve its training. This process can also occur intraoperatively. To accomplish this, we plan to develop an intraoperative user interface based on voice recognition and special labeling probe. A surgeon would be able to interact with the AOA using voice activation to ask questions of the AOA (i.e. "How certain are you that this is the disc material?", "How safe is it to retract this part of the thecal sac?") or ask the AOA to label objects as the user sees fit (i.e. "Label this object as the carotid artery."). Intraoperative feedback from the surgeon can also be fed back into the network to improve its output.

In the future, we foresee this technology being used on a digital, augmented reality enhanced, optical zoom capable surgical loupe headset where the video feed and subsequent visual feedback could be captured by and returned to the surgical loupe headset. As surgical headset technology improves, this type of AI system could become part of the surgical headpiece worn by every surgeon. This wide-reaching application of real-time, automated decision-making augmentation, surgical roadmaps, complication avoidance warnings, procedural stepwise cost estimates, predictive analytics, and tailored surgical guidance using artificial intelligence for surgeons is entirely novel; and our innovative AOA could redefine the forefront of cutting-edge surgical care. This technology also has the potential to transform surgical training and medical education. Trainees would gain valuable knowledge about anatomy and the operative field that most often takes years to hone. Medical students would be able to observe surgeries with the output of the AOA overlaid to improve their learning of anatomy.

Figure 1A:
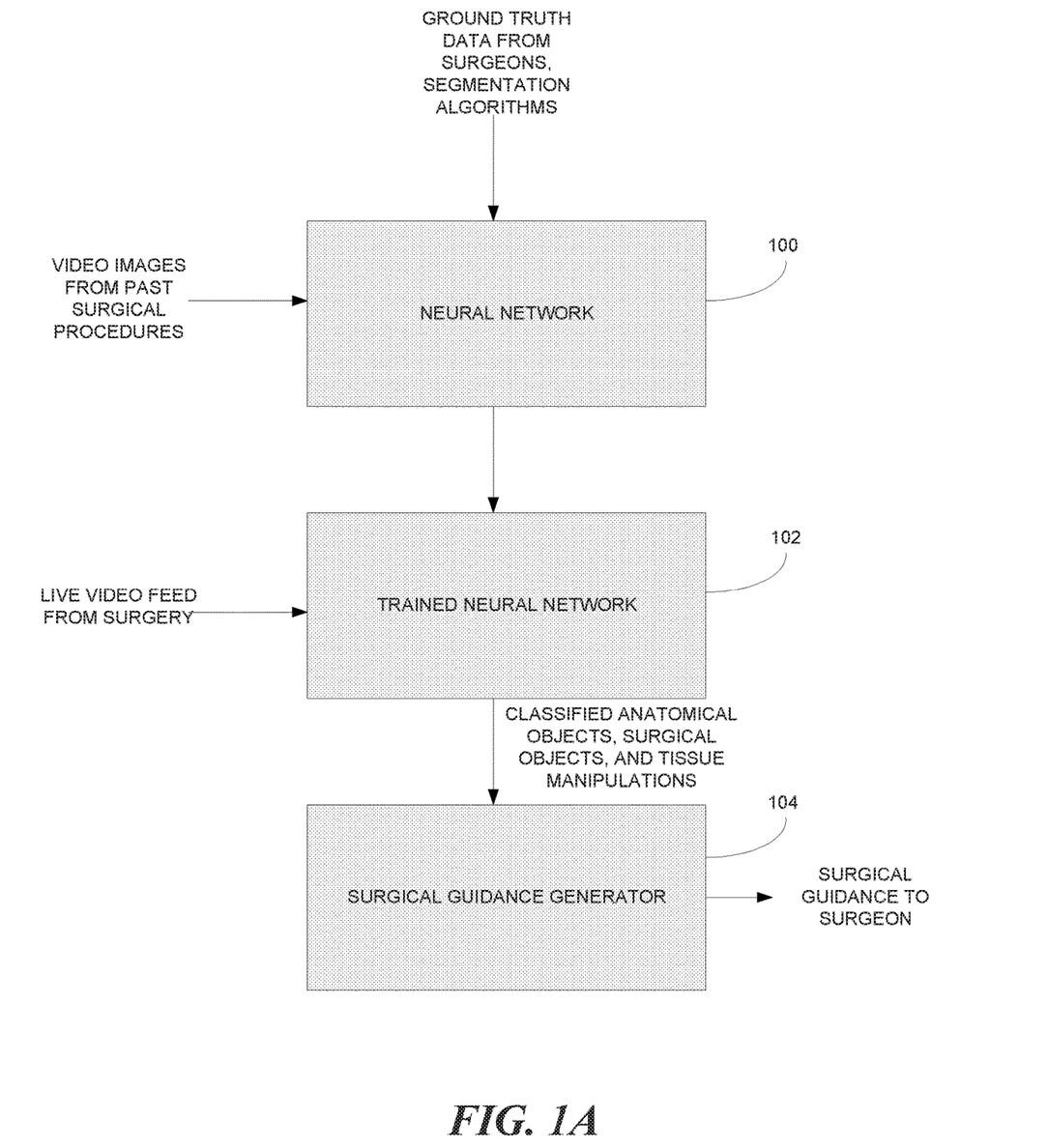
FIG. 1A is a block diagram of a system for generating and providing artificial intelligence assisted surgical guidance.

FIG. 1A is a diagram illustrating exemplary systems for AI assisted surgical guidance. Referring to FIG. 1A, a neural network 100 may be trained from video images from past surgeries and ground truth data from surgeons to identify anatomical objects, surgical objects, and tissue manipulations in the video images. The result of the training is a trained neural network 102 that is trained to identify anatomical objects, surgical objects, and tissue manipulations.

Trained neural network 102 receives a live video feed from the surgery and outputs classifications of anatomical objects, surgical objects, and tissue manipulations. This information is output to a surgical guidance generator 104, which post-processes the neural network data through novel hierarchical algorithms to generate and output surgical guidance to a surgeon in real time during surgery. In the most basic example, the surgical guidance may be the anatomical object surgical object, or tissue manipulation classifications superimposed on the regions of the images where these objects appear.

Figure 1B:
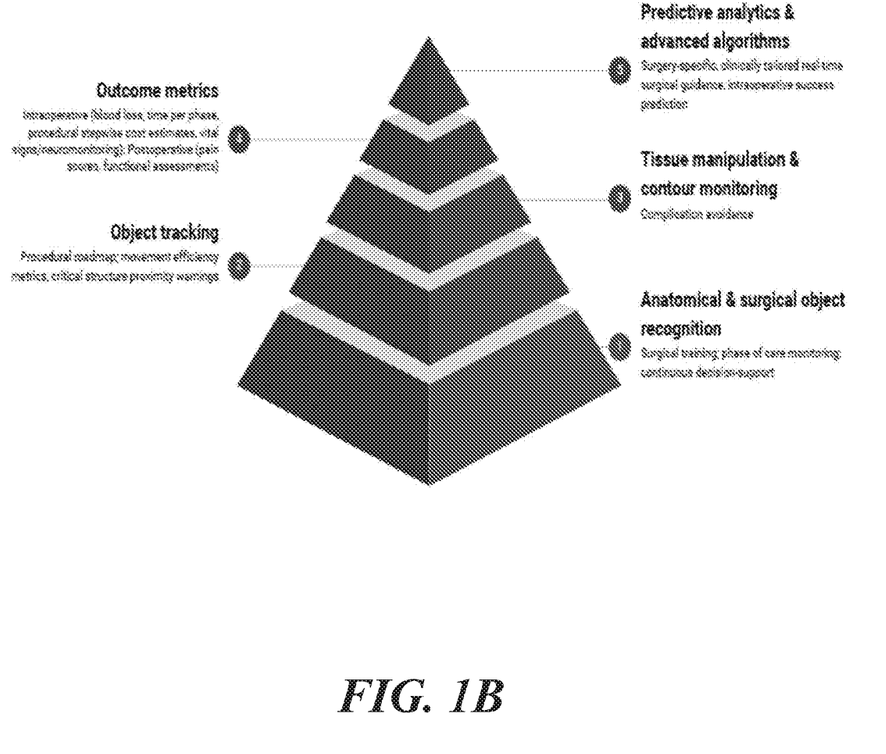
FIG. 1B is a diagram illustrating a hierarchy of functions performed by the surgical guidance generator illustrated in FIG. 1A.

FIG. 1B is a diagram illustrating a hierarchy of functions performed by the surgical guidance generator illustrated in FIG. 1A. At the lowest level of the hierarchy, anatomical and surgical objects are identified. At the next level, movement of the anatomical and surgical objects is tracked. At this level critical structure proximity warnings along with procedural next-step suggestions may be generated. At the next level in the hierarchy, tissue manipulation and contour monitoring are performed to warn the surgeon about complications that may result from manipulating tissue beyond safe mechanical ranges. At the next level in the hierarchy, intraoperative outcome metrics may be generated and utilized to create feedback to the surgeon. Examples of intraoperative outputs that may be generated include blood loss, time per phase, procedural stepwise cost estimates, vital signs, and neuromonitoring data. Similarly, postoperative metrics may also be correlated and utilized to create feedback to the surgeon. These postoperative metrics may include pain scores and functional assessments. At the next level in the hierarchy, predictive analytics and advanced algorithms may be used to generate and output surgery specific, clinically tailored real time surgical guidance and an intraoperative prediction of success of a surgical procedure. Specific examples of output that may be generated by the system illustrated in FIG. 1A will now be described.

In one example, neural network 100 may be trained to identify bone, muscle, tendons, organs, blood vessels, nerve roots, as well as abnormal tissues, including tumor.

In another example, neural network 100 may be trained to identify changes in contour of specific tissue types. In such a case, surgical guidance generator 104 may output a warning when a change in contour for tissue type identified in the live video feed nears a damaged threshold for the tissue type. Such output may prevent the surgeon from damaging tissue during the surgery.

In another example, neural network 100 may be trained to identify and track changes in anatomical objects, surgical objects, and tissue manipulations over the course of surgical procedures and over time.

In another example, neural network 100 may be trained to identify a pointer instrument having a pointer end that when brought in close proximity to a tissue type in the live video feed triggers surgical guidance generator 104 to generate output identifying the tissue type. For example, when the pointer is brought in close proximity to bone, surgical guidance generator 104 may generate output indicating the word "bone" superimposed on the bone tissue in the live video feed, or as an auditory signal saying the word "bone", during the surgery. When using surgery-specific anatomical object outputs, "bone" could be replaced by a more specific anatomical structure seen in the given operation, such as "lamina" or "facet joint" during spine surgery.

In another example, algorithms that process and display output from neural network 102 in surgery and surgeon-specific manners may be used in combination with trained neural network 102 to provide enhanced surgical guidance. This can include a surgical roadmap with suggested next steps at each time point based on chronologically processed data for each surgery type, or a continuous extent-of-resection calculation for tumor resection surgery by utilizing volumetric analysis of the resection cavity in real-time. Surgeon-specific metrics could include movement efficiency metrics based on, for example, the amount of time a particular instrument was used for a given step in the procedure. The surgeon could use this type of active feedback over time to improve their own operative efficiency. Cost information of various surgical objects could also be incorporated to enable active feedback of cost during each step to reduce behaviors leading to surgical waste.

In yet another example, surgical guidance generator 104 may process data from multiple input sources, including pre-operative imaging, patient-specific risk factors, and intraoperative vital signs and output such data superimposed on the live video feed of the surgery to provide surgical guidance to the surgeon.

Surgical guidance generator 104, in one example, may output the surgical guidance on a video screen that surgeons use during image guided surgery. The video screen may be standalone display separate from the surgical field or an augmented reality display located in or in front of the surgical field.

Figure 2:
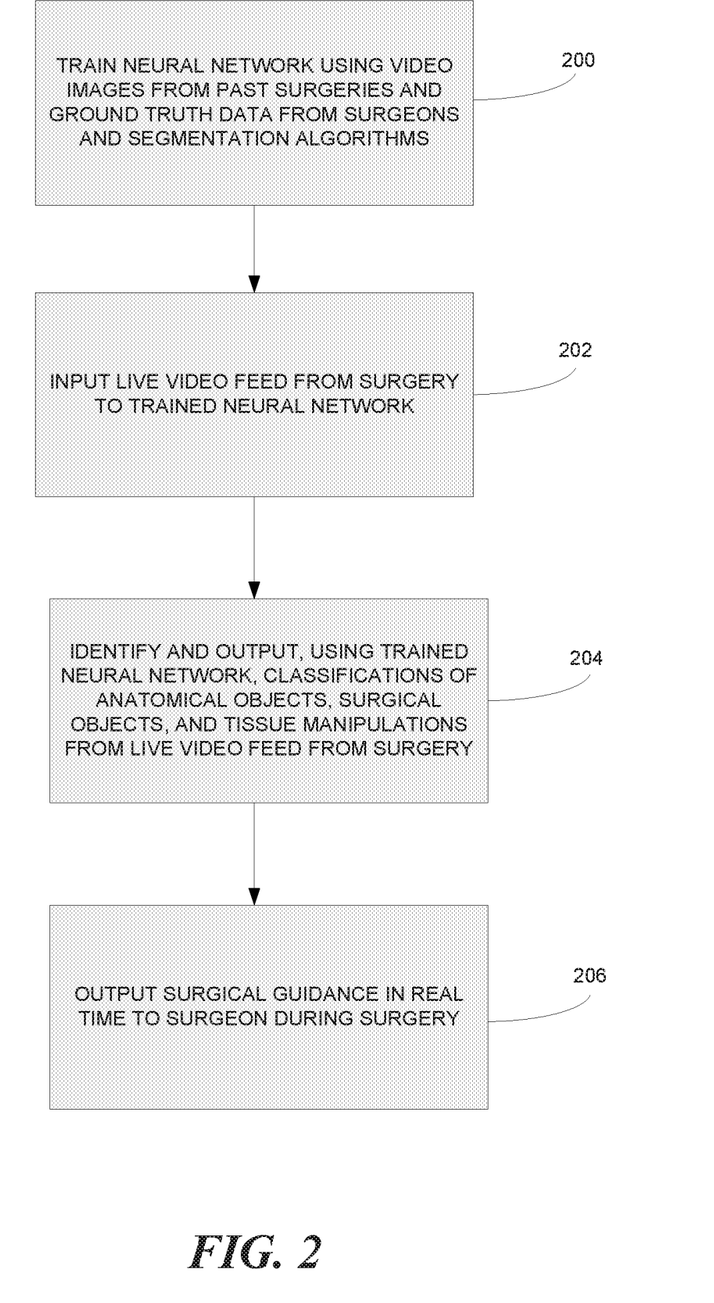
FIG. 2 is a flow chart illustrating an exemplary process for generating and providing artificial intelligence assisted surgical guidance.

FIG. 2 is a flow chart illustrating an exemplary process or providing artificial intelligence assisted surgical guidance. Referring to FIG. 2, in step 200, video images from surgical procedures are analyzed and used to train a neural network to identify at least one of anatomical objects, surgical objects, and tissue manipulations in the video images. For example, neural network 100 may be trained using video images from past surgeries and ground truth data from surgeons and/or segmentation algorithms that identify anatomical objects, surgical objects, and tissue manipulations in the video images. In step 202, the neural network may receive a live feed of video images from a surgery in progress. For example, trained neural network 102 may be provided with live video feed from a surgery.

In step 204, trained neural network 102 identifies anatomical objects, surgical objects, and tissue manipulations from the live video feed from the surgery and outputs classifications of the anatomical objects, surgical objects, and tissue manipulations. For example, trained neural network 102 may output the classifications to surgical guidance generator 104 illustrated in FIG. 1A.

In step 206, surgical guidance may be generated based on the classified anatomical objects, surgical objects, and tissue manipulations in the live video feed. For example, surgical guidance generator 104 may output surgical guidance to surgeons based on anatomical objects, surgical objects, and tissue manipulations classified by trained neural network 102. In addition, the surgical guidance may include data from other sources, such as pre-operative images or other patient or surgery specific data.

Figure 3A:
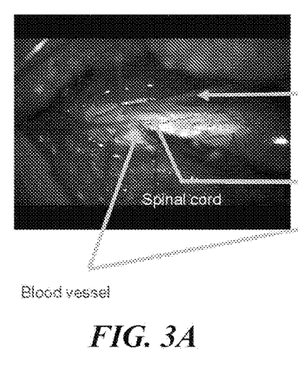
FIGS. 3A-3C are examples of: A) a training video image; B) a labeled image produced from the training image; and C) the labeled image overlaid on the training image.
Figure 3B:
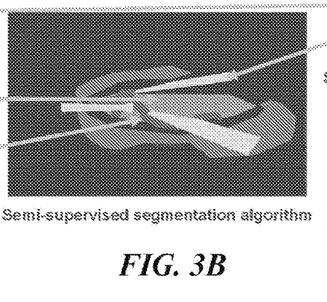
Figure 3C:
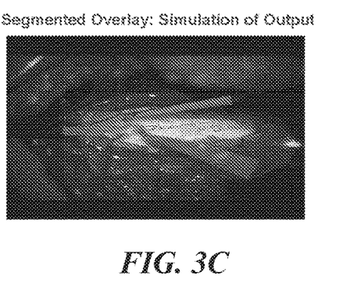

FIGS. 3A through 3C illustrate exemplary training of neural network 100. More particularly, FIG. 3A illustrates an image of an abnormal blood vessel around the spinal cord from a video taken during a surgery. FIG. 3B illustrates segmentation of the image in FIG. 3A identifying a surgical instrument, the spinal cord, and the blood vessels. FIG. 3C illustrates an overlay of the segmentation and the image of the blood vessel. The segmentation data in FIG. 3B may be used to train neural network 100 to identify the anatomical objects (the blood vessel and the spinal cord) and the surgical instrument. Once trained, the neural network can output segmented overlays, such as that illustrated in FIG. 3C.

Figure 4:
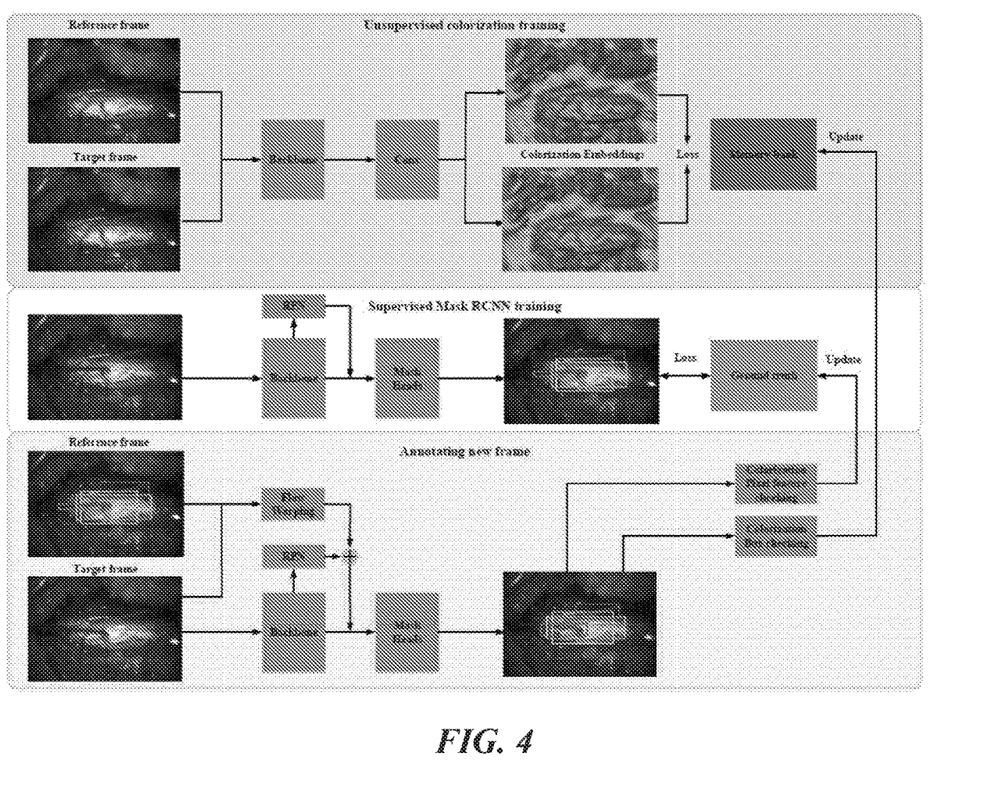
FIG. 4 is a diagram of the custom neural network processing pipeline for monitoring surgical video frames over time to segment and track anatomical objects, surgical instruments, and interfaces between different anatomical objects and between the instruments and the anatomical objects.

FIG. 4 is a diagram of the custom neural network processing pipeline for monitoring surgical video frames over time to segment and track anatomical objects, surgical instruments, and interfaces between different anatomical objects and between the instruments and the anatomical objects. In FIG. 4 the topmost rectangle labeled unsupervised colorization training illustrates unsupervised training of a convolutional neural network to identify object contours based on color properties of the images. The inputs to convolutional neural network are a target frame and a reference frame, where the reference frame is a frame depicting a surgical field at a first time point and the target frame is a frame depicting the surgical field at a second time point after the first time. The boxes labeled Backbone and Cony represent the convolutional neural network being trained. The convolutional neural network backbone may be modified from the Detectron mask recurrent convolutional neural network (mask RCNN) made available by Facebook at https://github.com/facebookresearch/Detectron or other publicly available Python-based CNNs.

Continuing with the unsupervised training rectangle in FIG. 4, the outputs of the neural network are colorizations of the reference frame and the target frame, where likely object contours are defined in terms of color data. The loss represents the difference in colorization between the colorization produced from the reference frame and the colorization produced from the target frame. Over numerous video frames this unsupervised algorithm creates a memory bank of sequential colorization embeddings which can then be used to inform the outputs of the trained custom neural network The central rectangle in FIG. 4 represents supervised training of the mask RCNN using ground truth image data labeled by surgical experts. Because there can be thousands of image frames in every surgery and manual labeling of surgical images is time consuming and requires a surgical expert, it is desirable to only manually label a subset of images from a surgery to train the RCNN. In the supervised training of the RCNN, the RCNN receives as input an image to be classified and ground truth data including one or more labeled surgical images frames. A region proposal network (RPN) receives image data from the backbone and outputs proposed regions of interest to inform object segmentation. The mask heads create proposed labels for anatomical objects in the image to be classified. The RCNN produces a surgical image with instance segmentations around classified anatomical structures and surgical instruments. The RCNN also outputs a loss indicative of a difference between the network-classified and manually classified image.

The lowermost rectangle in FIG. 4 represents the semi-supervised annotation of a target frame with unknown anatomical objects and/or surgical instruments using the sparsely trained RCNN. In the lowermost rectangle, the RCNN receives as input the target frame to be classified. A flow warping algorithm calculates the movement trajectory of each segmented object from the preceding frames to guide the RPN in choosing regions of interest. The mask RCNN segments the target frame. The output is checked against the memory bank to refine network outputs. This is in turn used to update the suggested pixel-wise object contours and bounding box contours stored in the memory bank. Thus, the system illustrated in FIG. 4 learns as it classifies each new image. This process enables a methodology to minimize manual labeling of surgical data while still enabling high classification accuracy of the custom neural network outputs.

Figure 5:
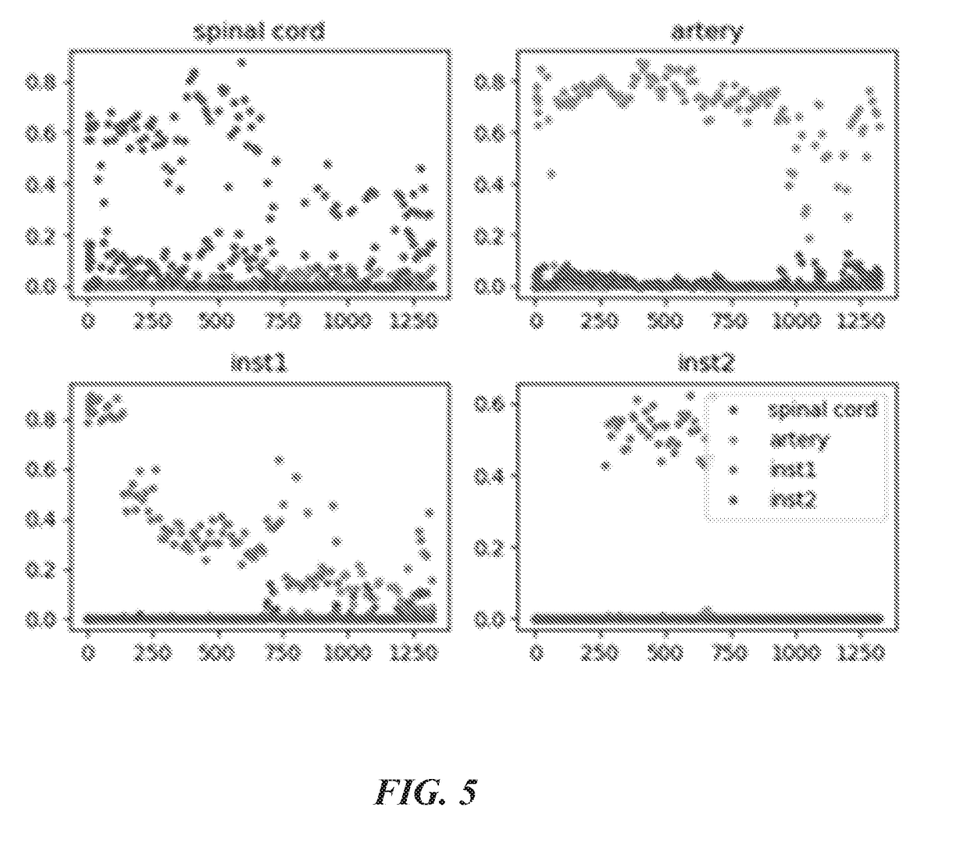
FIG. 5 includes intersection over union (IoU) graphs illustrating classification accuracy of the architecture illustrated in FIG. 4.

FIG. 5 includes intersection over union (IoU) graphs illustrating classification accuracy of the architecture illustrated in FIG. 4. In FIG. 5, the horizontal axis of each graph represents different frames over time. The vertical axis represents intersection over union, which is a measure of percentage accuracy of the classification. The upper left graph in FIG. 5 shows classification accuracy of the spinal cord clustered mainly between 60% and 80%. The upper right graph in FIG. 5 shows similar accuracy for classification of an artery. The lower graphs illustrate classification accuracy for a first instrument, labeled instr1 that begins about 80% and decreases over time. The classification of inst2 zero, due to the co-classification of instrument 1 and instrument 2.

Figure 6A:
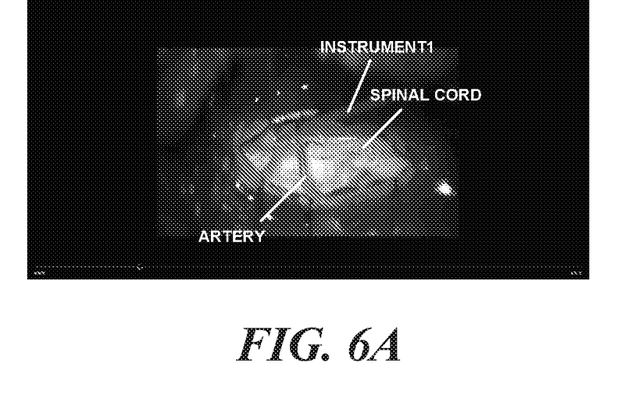
FIGS. 6A and 6B are computer screen captures of surgical video frames at different times illustrating automated segmentation of anatomical objects and surgical instruments using the architecture illustrated in FIG. 4.
Figure 6B:
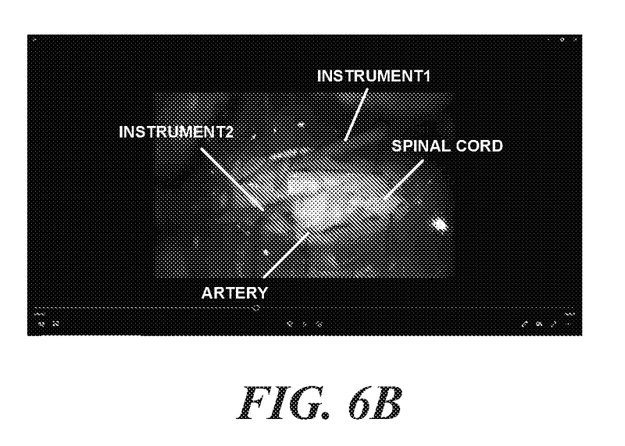

FIGS. 6A and 6B are computer screen shots of surgical video frames at different times illustrating segmentation of anatomical objects and instruments using the architecture illustrated in FIG. 4. The textual labels in FIGS. 6A and 6B were added manually for illustrative purposes but could have been added by the network illustrated in FIG. 4. In FIG. 6A, the video frame shows an artery, the spinal cord, and an instrument, labeled INSTRUMENT1. The artery, spinal cord and INSTRUMENT1 are segmented by the network illustrated in FIG. 4, and that segmentation is depicted in the video frames as transparent color of different colors on top of each anatomical object or image. For example, the artery may be overlaid with a blue transparent overlay, the spinal cord may be overlaid with a yellow transparent overlay, and the instrument may be overlaid with a purple transparent overlay. FIG. 6B illustrates a subsequent video frame and how the segmentation performed by the network illustrated in FIG. 4 tracks movement of the anatomical objects and instruments. In FIG. 6B, the artery has been moved to a new position by a second instrument, labeled INSTRUMENT2. Thus, the trained RCNN illustrated in FIG. 4 segments anatomical objects and surgical instruments in a live video feed from surgery and tracks movements of the instruments and anatomical objects over time.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A system for generating and providing artificial intelligence assisted surgical guidance, the system comprising:
   at least one processor;
   a neural network implemented by the at least one processor and trained through analysis of video images from surgical procedures to identify at least one of anatomical objects, surgical objects, and tissue manipulations in the video images;
   the neural network being configured to receive, a live feed of video images from a surgery and classify at least one of anatomical objects, surgical objects, and tissue manipulations in the live feed of video images, wherein the neural network includes a backbone comprising a mask-recurrent convolutional neural network (mask RCNN) that receives, as input, a target frame from the live feed of video images and generates as output, image data including a colorization of the target frame that defines likely object contours in terms of color data, the neural network further includes a region proposal network (RPN) that receives, as input, the image data output from the backbone and generates, as output, proposed regions of interest for informing object segmentation, and the neural network further includes mask heads that receive the output from the backbone and the RPN and generates, as outputs, labels for the at least one of the anatomical objects, the surgical objects, and the tissue manipulations in the target frame; and
   a surgical guidance generator implemented by the at least one processor for outputting, in real time, guidance based on the classified at least one of anatomical objects, surgical objects, and tissue manipulations in the live feed of video images, wherein outputting the guidance includes overlaying the labels for the at least one of the anatomical objects, the surgical objects, and the tissue manipulations on the live feed of video images or onto a surgical field using augmented reality.

2. The system of claim 1 wherein the neural network is trained to identify tissue including bone, muscle, tendons, organs, blood vessels, and nerve roots, as well as abnormal tissues including tumor.

3. The system of claim 1 wherein the neural network is trained to identify changes in contour of specific tissue types and wherein the surgical guidance generator is configured to output a warning when a change in contour for a tissue type identified in the live video feed nears a damage threshold for the tissue type.

4. The system of claim 1 wherein the neural network is trained to identify and track changes over time and across multiple surgical procedures in at least one of anatomical objects, surgical objects, and tissue manipulations.

5. The system of claim 1 wherein the neural network is trained to identify a pointer instrument having a pointer end that when brought in close proximity to an anatomical object in a live feed of video from a surgery triggers the surgical guidance generator to generate output identifying the anatomical object.

6. The system of claim 1 wherein the surgical guidance generator is trained to interact with a surgeon using voice recognition.

7. The system of claim 1 wherein outputting the surgical guidance displaying movement efficiency metrics and intra-operative metrics predicting success of each surgery.

8. The system of claim 1 wherein outputting the surgical guidance includes incorporating information from additional sources including pre-operative imaging, patient-specific risk factors, surgical object cost data, and intraoperative vital signs.

9. The system of claim 1 wherein mask recurrent convolutional neural network is trained by performing semi-supervised training of the mask recurrent neural network to detect patterns of the at least one of anatomical objects, surgical objects and tissue manipulations in the video frames in combination with supervised training of the mask recurrent convolutional neural network using labeled surgical image frames.

* * * * *